United States Patent
Ueno

(10) Patent No.: US 6,596,765 B2
(45) Date of Patent: Jul. 22, 2003

(54) TREATMENT OF OCULAR HYPERTENSION AND GLAUCOMA

(75) Inventor: Ryuji Ueno, Potomac, MD (US)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 09/851,111

(22) Filed: May 9, 2001

(65) Prior Publication Data

US 2002/0035149 A1 Mar. 21, 2002

Related U.S. Application Data

(63) Continuation-in-part of application No. 09/734,692, filed on Dec. 13, 2000, now abandoned, which is a continuation-in-part of application No. 09/620,416, filed on Jul. 20, 2000, now abandoned.

(51) Int. Cl.$^7$ .............................................. A61K 31/215
(52) U.S. Cl. ...................... 514/530; 514/573; 514/913
(58) Field of Search ................... 514/530, 573, 514/912, 913

(56) References Cited

U.S. PATENT DOCUMENTS

| | | |
|---|---|---|
| 5,296,504 A | 3/1994 | Stjernschantz et al. |
| 5,321,128 A | 6/1994 | Stjernschantz et al. |
| 5,422,368 A | 6/1995 | Stjernschantz et al. |
| 5,422,369 A | 6/1995 | Stjernschantz et al. |
| 5,578,618 A | 11/1996 | Stjernschantz et al. |
| 5,627,208 A | 5/1997 | Stjernschantz et al. |
| 5,849,791 A | 12/1998 | Stjernschantz et al. |
| 6,030,999 A | 2/2000 | Stjernschantz et al. |

OTHER PUBLICATIONS

Tsuyoshi Habe et al. "Role of the Intraocular Metabolite in Intraocular Pressure Reducing Effect of Prostaglandin $F_2\alpha$ Analogue Latanoprost in Monkeys" Clinical Report vol. 28. No. 11: 3505–3509 Oct. 1994 and translation.

Hiroyoshi Osama "Comparatie study of intraocular pressure lowering effects of 0.005% latanoprost and 0.005% 15–keto– latanoprost in monkeys" Study No. YG–Oc–5056 and translation, 1994.

Hiroyoshi Osama "Intraocular pressure lowering effect of 15–keto acid of latanoprost by perfusion in the anterior chamber of monkeys" Study No. YG–Oc–5057 and translation, 1994.

Hiroyoshi Osama "Intraocular pressure lowering effect of 15–keto acid of latanoprost by intravitreal injection in normal monkeys" Study No. YG–Oc–5058 and translation, 1994.

Tsuyoshi Habe "Metabolite concentration profiled in aqueous humor following an ocular administration of$^3$–H–Latanoprost in monkey" Study No.: MRLata99001 and translation, 1994.

Tohru Hirato and Tetsuo Deguchi "Effects of intra–anterior chamber perfusion with 2 ng/mL solution of 13,14–dihydro–15–keto–17–phenyl–18,19,20–trinor– $PGF_2\alpha$ (15—keto acid of latanoprost) on intraocular pressure in monkeys" Study No. YG–Oc–5063 and translation, 1994.

Tetsuo Deguchi "Comparison of intraocular pressure lowering effects of 0.0005% 13,14–dihydro–15–keto–17–phenyl–18,19, 20–trinor–$PGF_2\alpha$–isopropyl ester (15–keto–latanoprost) and 0.0005% 13,14–dihydro–17–phenyl–18,19,20–trinor–$PGF_2\alpha$– isopropyl ester (latanoprost) in monkeys", Study No. YG–Oc–5062 and translation, 1994.

Hiroyoshi Osama "Investigation of signifcance of the presence of 13,14–dihydro–15–keto type metabolite produced from latanoprost in the eye after instillation of latanoprost intraocular pressure lowering maintenance effect of 15–keto–latanoprost" Study No. YG–Oc–5060 and translation, 1994.

*Primary Examiner*—Zohreh Fay
(74) *Attorney, Agent, or Firm*—Sughrue Mion, PLLC

(57) ABSTRACT

15-keto latanoprost and other 15-keto prostaglandin analogs are used as ocularly applied intraocular pressure reducing agents.

17 Claims, 3 Drawing Sheets

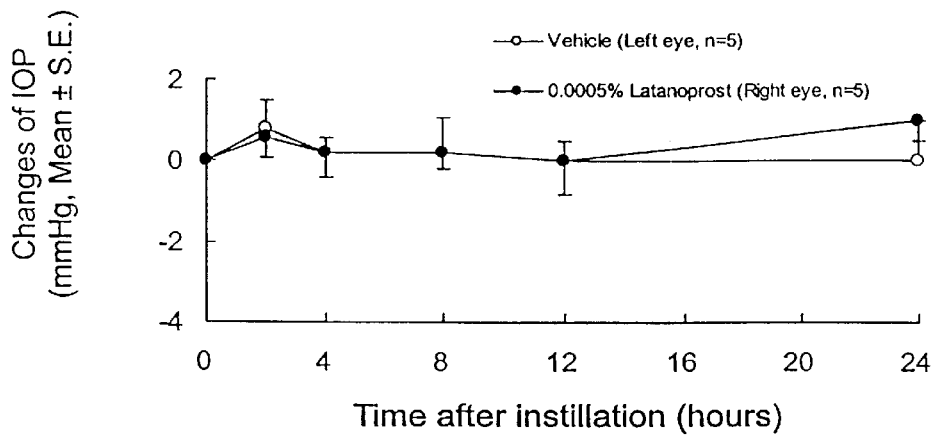

Fig. 1 Effect of 0.0005% latanoprost on intraocular pressure (IOP) in monkeys
Latanoprost was instilled into the right eye. The left eye received the vehicle.
No significant difference between the latanoprost-treated eye and the vehicle-treated contralateral eye (Student's t-test).

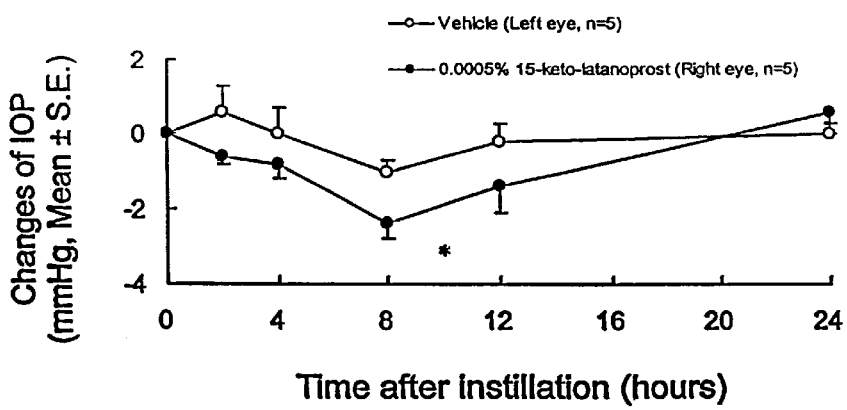

Fig. 2 Effect of 0.0005% 15-keto-latanoprost on intraocular pressure (IOP) in monkeys
15-keto-latanoprost was instilled into the right eye. The left eye received the vehicle.
*$p < 0.05$ compared with the vehicle-treated contralateral eye (Student's t-test).

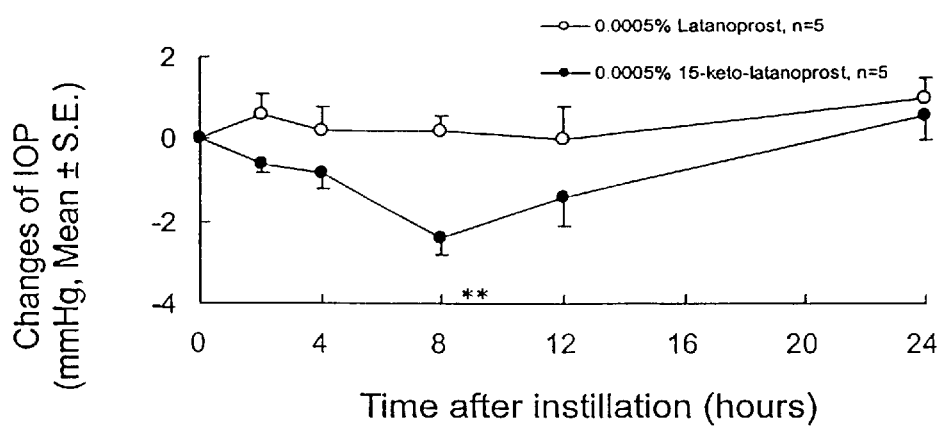
Fig. 3 Effects of 0.0005% 15-keto-latanoprost and 0.0005% latanoprost on intraocular pressure (IOP) in monkeys
**p < 0.01 compared with 0.0005% latanoprost-treated group (Student's t-test).

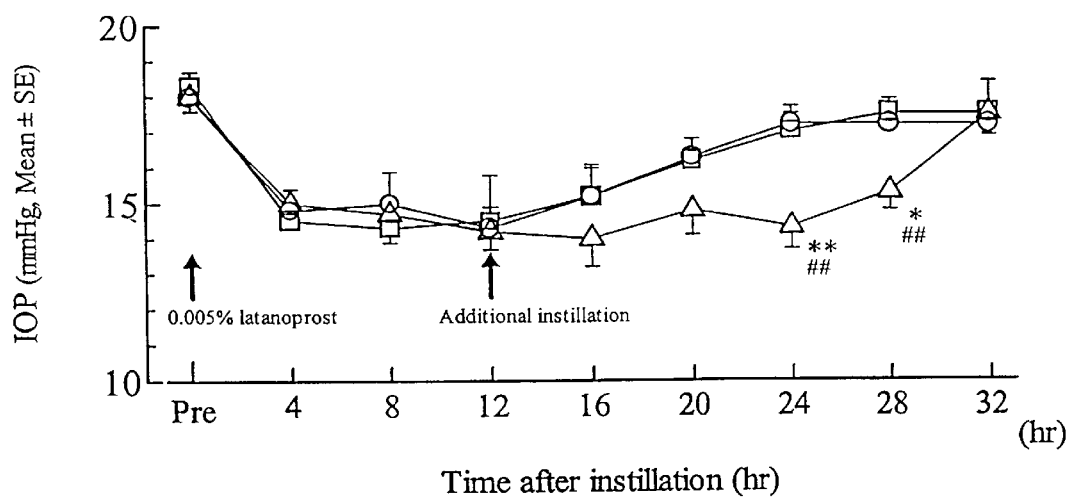

Fig. 4 Effects of single instillation of 0.005% latanoprost, additional instillation of 0.0005% latranoprost 12 hours after instillation of 0.005% latanoprost and additional instillation of 0.0005% 15-keto-latanoprost 12 hours after instillation of 0.005% latanoprost on intraocular pressure (IOP) in monkeys O     0.005% latanoprost alone (n=6)
□     0.005% latanoprost + 0.0005% latanoprost (n=6)
Δ     0.005% latanoprost + 0.0005% 15-keto-latanoprost (n=6)
mean ± S.E.
    *p<0.05, ** p<0.01 as compared with 0.005% latanoprost alone     } Turkey's Comparison
    ## p<0.01 as compared with 0.005% latanoprost + 0.0005% latanoprost

TREATMENT OF OCULAR HYPERTENSION AND GLAUCOMA

This application is a Continuation-In-Part of U.S. application Ser. No. 09/734,692, filed Dec. 13, 2000, now abandoned, in turn a Continuation-in-Part of U.S. application Ser. No. 09/620,416, filed Jul. 20, 2000 now abandoned.

BACKGROUND OF THE INVENTION

The prior art describes the use of prostaglandin analogs containing a ring structure in the omega chain for reducing intraocular pressure. A representative patent in this area is U.S. Pat. No. 5,321,128 to Stjernschantz. These compounds contain a hydroxy group or keto group as a substituent at the 15-position. Also, one subset of these compounds contains an unsubstituted phenyl group substituted on carbon atom number 17 of the omega chain and the absence of carbons 18–20. These types of structures, where the conventional prostaglandin carbons 18–20 and their equivalent are absent are named by Stjernschantz as 18,19,20-trinor prostaglandins.

One of the above-described type of compounds, latanoprost, is now sold commercially as an IOP (intraocular pressure) reducing eye drop. The clinical dosage is 1.5 µg per dose as an eye drop, once a day. This is the U.S. FDA approved dosage. The provided liquid composition product can contain 0.005% latanoprost used at a dosage of one drop, or about 30 µl, providing 1.5 µg per dose. Latanoprost is named by Stjernschantz as 13,14-dihydro-17-phenyl-18,19,20-trinor-PGF$_2\alpha$ isopropyl ester.

Another compound of this family known to date is 13,14-dihydro-15-oxo-17-phenyl-18,19,20-trinor PGF$_2\alpha$ isopropyl ester, hereinafter referred to as 15-keto latanoprost.

The above noted patent describes a wide potential dosage range as therapeutically active. For example, see column 5, lines 33–66 of the '128 patent ("The composition contains about 0.1–30 µg, especially 1–10 µg, per application of the active substance . . . "). Even so, the lowest dosage used in the '128 patent for any test compound for evaluating IOP reduction in humans or monkeys is 1.0 µg per eye. For 15-keto latanoprost in the '128 patent, the tested dosage in healthy human volunteers is 5 µg per eye and is 3 µg in the monkey eye. Latanoprost is tested in the '128 patent at a dosage of 1.0 µg per eye in healthy human volunteers and at a dosage of 10.4 µg in the monkey eye.

Latanoprost at its clinical concentration can cause pigmentation of the iris, a mild IOP spike and/or mild hyperemia.

SUMMARY OF THE INVENTION

It has been discovered that 15-keto latanoprost can be used in an unusually low dosage for reduction of IOP. Another embodiment of the present invention is the use of 15-keto latanoprost at a dosage up to about the clinical dosage of latanoprost. 15-keto latanoprost does not cause iridic pigmentation, an initial IOP spike nor any hyperemia at the dosages described herein. Still another embodiment of the present invention is the use of 15-keto latanoprost for maintaining IOP reduction over an extended time following an initial rapid IOP reduction bought about by another IOP reducing agent, such as latanoprost.

The embodiments of the present invention involve treatment of glaucoma where IOP reduction is needed and the lowering of IOP for purposes other than treatment of glaucoma.

This application describes other 15-keto prostaglandins useable at low dosages for treating ocular hypertension and glaucoma.

DESCRIPTION OF THE DRAWING

FIGS. 1 and 2 set forth the results of Example 1 comparing the employment of a dose of 0.175 µg latanoprost (FIG. 1) and the same dose of 15-keto latanoprost (FIG. 2) in the monkey eye.

FIG. 3 is a graph depicting a comparison of the results for the active ingredients of Example 1 without the controls, as depicted in FIGS. 1 and 2.

FIG. 4 depicts the results of Example 2 where an additional instillation of a small amount of latanoprost or 15-keto lantanoprost is administered 12 hours after instillation of a clinical dose of latanoprost in the monkey eye.

DETAILED DESCRIPTION OF THE INVENTION

The present invention relates to the employment of varying, including small, ocular dosages of 15-keto latanoprost, and related 15-keto compounds, as an IOP reducing agent, administered topically to the eye in the treatment of glaucoma or ocular hypertension. The active agent is administered as a topically applied ocular composition, most usually in the form of a liquid eye drop.

The dose of 15-keto latanoprost is selected so that any side effects caused by the ocular application of prostaglandin analogs, including those which contain a ring such as latanoprost, are substantially completely eliminated. The effective dose exemplified herein can be as low as about one-tenth the clinical dose of latanoprost.

The ophthalmic vehicle employed in the practice of the present invention is that now know in the art for IOP reducing agents, such as the a-fore-mentioned latanoprost and Rescula®, the latter which has an extended omega chain providing a docosanoid classification. Additional information on ophthalmic vehicles is found in the patent noted in the background section of this patent application. Although 15-keto latanoprost is an isopropyl ester, it is contemplated that the free acid as well as pharmaceutically acceptable salts, ethers and other esters are potentially useful in the practice of the present invention, such as those described in the above-noted patent.

As noted above, the clinical dose for latanoprost is about 1.5 µg per eye. At one-tenth the clinical dose, latanoprost is essentially inactive. Quite surprisingly, 15-keto latanoprost is an effective IOP reducing agent when used at about one tenth the clinical dose of latanoprost. It is contemplated in one embodiment of the present invention that the dosage range for 15-keto latanoprost as a topically applied ocular IOP reducing agent is about 0.100 to 0.750 µg/eye, preferably about 0.125 to 0.250 µg/eye, more preferably about 0.150 to 0.175 µg/eye. In another embodiment of the present invention, the dosage range for 15-keto latanoprost as a topically applied ocular IOP reducing agent is about 0.050 to below 5.0 µg/eye, or about 0.10 to 4.5 µg/eye, or about 0.50 to 2.5 µg/eye, or about 1.0 to 2.0 µg/eye.

EXAMPLE 1

This Example is an IOP test using the monkey eye in which about one tenth the clinical dose of latanoprost is compared in IOP reduction with the same dose of 15-keto latanoprost.

Summary

The intraocular pressure lowering effects of the 0.0005% solution of 13,14-dihydro-15-keto-17-phenyl-18,19,20-trinor-$PGF_{2\alpha}$-isopropyl ester (15-keto-latanoprost) and the 0.0005% solution of 13,14-dihydro-17-phenyl-18,19,20-trinor-$PGF_{2\alpha}$-isopropyl ester (latanoprost) were compared following a single, topical ocular instillation in monkeys.

No intraocular pressure lowering effect was noted following the instillation of 0.0005% latanoprost. On the other hand, the instillation of 0.0005% 15-keto-latanoprost lowered the intraocular pressure by 2.4 mmHg 8 hours after the administration as compared with the pre-treatment value. The reduction in the intraocular pressure by the instillation of 15-keto-latanoprost was statistically significant as compared with that by the instillation of the vehicle (contralateral eye) or of 0.0005% latanoprost.

These results indicate that 15-keto-latanoprost exerts a potent intraocular pressure lowering effect with a minute dose, and suggest that 13,14-dihydro-15-keto-17-phenyl-18,19,20-trinor-$PGF_{2\alpha}$ (15-keto acid of latanoprost) itself produced as a metabolite from latanoprost in the eyes participates in the reduction in the intraocular pressure after the instillation of latanoprost.

Materials and Methods

1. Test Substance 13,14-dihydro-15-keto-17-phenyl-18,19,20-trinor-$PGF_{2\alpha}$-isopropyl ester (15-keto-latanoprost)
13,14-dihydro-17-phenyl-18,19,20-trinor-$PGF_{2\alpha}$-isopropyl ester (latanoprost,)

2. Preparation of Dosing Solutions

The solution containing 15-keto-latanoprost or latanoprost at 0.0005% was prepared with the following vehicle. Composition of the vehicle[1] (/mL): NaCl (4.1 mg), $NaH_2PO_4$—$H_2O$ (4.6 mg), $Na_2HPO_4$—$2H_2O$ (5.94 mg), Benzalkonium Chloride (0.2 mg) and water for injection 3. Animals Five male cynomolgus monkeys purchased from Kasyo Co., Ltd. were used. These monkeys were housed individually in cages for monkeys in a room which was maintained at room temperature of 24±1° C., relative humidity of 55±10%, ventilation rate of about 12 times/hour and 12-hour light-dark cycle (fluorescent lighting: 8:00 a.m. to 8:00 p.m.). The animals were given food pellets for monkeys (PS, Oriental Yeast Co., Ltd.), vegetables and fruits, and allowed free access to tap water from an automatic dispenser. The healthy animals without abnormalities in the anterior segment of the eye were used in this study.

4. Test Groups and Administration Method

| Group | Administration method | Volume of administration | n |
|---|---|---|---|
| 15-keto-latanoprost 0.0005% | Instillation | 35 µL/eye | 5 |
| Latanoprost 0.0005% | Instillation | 35 µL/eye | 5 |

Five monkeys were divided into 2 groups of the group 1 (3 monkeys) and group 2 (2 monkeys). The 0.0005% 15-keto-latanoprost and 0.0005% latanoprost were instilled into the right eye of monkeys in the group 1 and 2, respectively. One week later, 0.0005% latanoprost and 0.0005% 15-keto-latanoprost were instilled into the right eye of monkeys in the group 1 and 2, respectively, in a crossover way. Thirty-five µL of each test solution was administered by use of a micropipet (Pipetman P 100, Gilson). To the left eye the same volume of the vehicle was administered. The intraocular pressure in each group before the instillation was as follows (in mmHg, mean±S.E.): the group receiving 15-keto-latanoprost; the right eye: 16.6±0.5, the left eye: 16.6±0.2, the group receiving latanoprost; the right eye: 15.8±0.7, the left eye: 17.0±0.3. There were no statistically significant differences between the values of the intraocular pressure before the instillation (Student's t-test).

5. Measurement of Intraocular Pressure

The animals were systemically anesthetized by an intramuscular injection of 5 mg/kg of ketamine hydrochloride (Ketalar®50, Sankyo Co., Ltd.), and the anterior segment of both eyes was anesthetized by a instillation of 0.4% oxybuprocaine hydrochloride (Benoxil® 0.4% solution, Santen Pharmaceutical Co., Ltd.). The animals were fixed in a sitting position, and the intraocular pressure was measured by use of an applanation pneumatonograph (Alcon Japan Ltd.) before, and 2, 4, 8, 12 and 24 hours after the instillation. The animals were kept in cages excepting the time of measurement of the intraocular pressure.

6. Statistical Analysis

The data were statistically analyzed with Student's t-test. P values less than 0.05 were considered to be statistically significant.

Results

The instillation of 0.0005% latanoprost did not lower the intraocular pressure (FIG. 1). On the contrary, the intraocular pressure in 0.0005% 15-keto-latanoprost-treated eye was lowered by 2.4 mmHg 8 hours after the instillation as compared with the pre-treatment value, and the reduction in the intraocular pressure was statistically significant as compared with that in the vehicle-treated contralateral eye (FIG. 2). In addition, as shown in FIG. 3, the reduction in the intraocular pressure with 0.0005% 15-keto-latanoprost was also statistically significant as compared with 0.0005% latanoprost.

Discussion

In the present study, the intraocular pressure lowering effects of latanoprost and 15-keto-latanoprost in monkeys were compared following a single instillation at 0.0005%, for about one-tenth the amount of clinically used latanoprost. While no reduction in the intraocular pressure was noted following the instillation of 0.0005% latanoprost, the instillation of 0.0005% 15-keto-latanoprost significantly lowered the intraocular pressure.

Above results clearly indicate that the potency of intraocular pressure lowering effect of 15-keto-latanoprost is significantly greater than that of latanoprost. Furthermore, the fact that 15-keto-latanoprost exerted a significant intraocular pressure lowering effect at such a low concentration, at which latanoprost had no effect, strongly suggests that 15-keto acid of latanoprost, a 13,14-dihydro-15-keto-type metabolite produced from latanoprost in the eyes, participates in the intraocular pressure lowering effect after the instillation of latanoprost.

References

1) Sjöquist B., et al.: Drug metabolism and disposition 26 (8): 745–754, 1998

EXAMPLE 2

This Example illustrates the employment of a low dose of 15-keto latanoprost for maintaining a low IOP level following single administration of another IOP reducing agent for obtaining a rapid drop in IOP.

Summary

The intraocular pressure in monkeys after single instillation of 0.005% latanoprost (clinical concentration) showed the maximum reduction at 12 hours after the instillation and thereafter the intraocular pressure recovered gradually and returned to the predosing level at 24 hours after the instillation. No difference was found between changes in intraocular pressure after additional instillation of 0.0005% latanoprost (the concentration: $\frac{1}{10}$ of latanoprost 0.005%) at 12 hours after instillation of 0.005% latanoprost and those after single instillation of 0.005% latanoprost. On the other hand, when 0.0005% 15-keto-latanoprost was additionally instilled at 12 hours after instillation of 0.005% latanoprost, the intraocular pressure was significantly maintained continuously at low levels as compared with that when 0.005% latanoprost alone was instilled or that when 0.0005% latanoprost was instilled additionally at 12 hours after instillation of 0.005% latanoprost. These results suggest that 15-keto acid of latanoprost, a 13,14-dihydro-15-keto type metabolite, produced from latanoprost in the eye after instillation of latanoprost participates in the maintenance of the intraocular pressure lowering effect after instillation of latanoprost.

I. Introduction

In the present study, the animals were treated by the instillation with latanoprost at the clinical concentration alone, or additional instillation of a small amount of latanoprost or 15-keto-latanoprost 12 hours after instillation of latanoprost when the IOP showed the maximum reduction after instillation of latanoprost. The changes of IOP in 3 different treatment groups were compared to investigate the significance of the presence of 15-keto acid of latanoprost, a 13,14-dihydro-15-keto type metabolite, in maintaining the IOP lowering effect observed after instillation of latanoprost.

II. Materials and Methods

1. Test Substance 15-keto-latanoprost and latanoprost which were synthesized in Ueno Institute for Medical Science were used.

2. Animals

Six male cynomolgus monkeys (body weight: 3.2–3.8 kg) were used. These monkeys were housed individually in cages for monkeys in a monkey rearing room which was maintained at room temperature of 24±1° C., relative humidity of 55±10%, and ventilation of about 12 times/hour and a 12-hour light-dark cycle (fluorescent lighting: 8:00 a.m. to 8:00 p.m.). The animals were given solid food for monkeys (PS, Oriental Yeast Co., Ltd.), vegetables and fruits, and allowed free access to tap water from an automatic dispenser. The healthy animals without abnormalities in the anterior segment were used in this study.

3. Preparation of Dosing Solution 0.0005% and 0.005% latanoprost eye drops and 0.0005% 15-keto-latanoprost eye drops were prepared with a vehicle consisting of the following composition. The composition of the vehicles in 1 mL was as follows: sodium chloride (4.1 mg), sodium hydrogenphosphate-1$H_2O$ (4.6 mg), disodium hydrogenphosphate-2$H_2O$ (5.94 mg), benzalkonium chloride (0.200 mg) and water for injection (1 mL).

4. Administration Method of Test Substance

In the present study, changes in IOP after instillation of 0.005% latanoprost alone at the clinical concentration were compared with those in IOP after additional instillation of 0.0005% latanoprost or 0.0005% 15-keto-latanoprost 12 hours after instillation of 0.005% latanoprost to investigate the significance of the presence of a 13,14-dihydro-15-keto type metabolite in maintaining the IOP lowering effect observed after instillation of latanoprost.

The following 3 treatments were given to the right eye of monkeys at the intervals of at least 10 days. Namely, (1) instillation of 0.005% latanoprost alone, (2) additional instillation of 0.0005% latanoprost at 12 hours after instillation of 0.005% latanoprost, and (3) additional instillation of 0.0005% 15-keto-latanoprost at 12 hours after instillation of 0.005% latanoprost. Thirty $\mu$L of each test substance was instilled into the right eye of animals with a Pipetman (Gilson). The same amount of the vehicle was instilled into the left eye.

5. Measurement of IOP

After the ocular surface of monkeys was anesthetized with 0.4% oxybuprocaine hydrochloride (Benoxil® 0.4% solution, Santen Pharmaceutical Co., Ltd.) under i.m. systemic anesthesia with 5–7.5 mg/kg of ketamine hydrochloride, IOP was measured with an applanation pneumatonograph (Alcon Japan Ltd.). IOP was measured before instillation and at 4, 8, 12, 16, 20, 24, 28 and 32 hours after instillation of 0.005% latanoprost.

III. Results

As FIG. 4 shows, when 0.005% latanoprost alone was instilled into the eye of monkeys, IOP decreased with time at 4, 8 and 12 hours after instillation. The IOP returned with time toward the predosing levels at 16 and 20 hours after instillation of 0.005% latanoprost. IOP returned toward the predosing levels at 24 hours after instillation.

Additional instillation of 0.0005% latanoprost at 12 hours after instillation of 0.005% latanoprost did not affect IOP as compared with that after instillation of 0.005% latanoprost alone.

On the other hand, the IOP was maintained at significantly low levels when 0.0005% 15-keto-latanoprost was additionally instilled at 12 hours after instillation of 0.005% latanoprost as compared with that when 0.005% latanoprost alone was instilled, or that when 0.0005% latanoprost was additionally instilled 12 hours after instillation of 0.005% latanoprost.

These results indicate that the IOP lowering effect after instillation of latanoprost is prolonged markedly by additional instillation of a small amount of 15-keto-latanoprost.

Other 15-keto prostaglandins which should be useful in the practice of the present invention are 15-oxo-16-(3-trifluoromethyl phenoxy)-17,18,19,20-tetranor $PGF_2\alpha$ and 13,14-dihydro-15-oxo-16-(3-trifluoromethyl phenoxy)-17,18,19,20-tetranor $PGF_2\alpha$ isopropyl esters. The corresponding pharmaceutically acceptable salts, ethers, other esters and amides should be useful in the practice of the present invention. See U.S. Pat. No. 5,510,383 for the corresponding 15-OH compound. The clinical (once a day) dosage (FDA approved dosage) for 16-(3-trifluoromethyl phenoxy)-17,18,19,20-tetranor $PGF_2\alpha$ isopropyl ester is one drop of a 0.004% solution. Drop size can range from about 20 to 50 $\mu l$, typically about 30 to 35 $\mu l$. Thus, applicant as of this writing estimates the clinical dosage of this compound to be within the range of 0.8 to 2.0 $\mu g$/eye, probably about 1.2 $\mu g$/eye. The low dosage contemplated herein for these compounds as the isopropyl ester is below 0.2 $\mu g$/eye, to as low as 0.03 $\mu g$/eye. In another embodiment of this invention, these two isopropyl ester compounds are topically applied to the eye in a dosage of about 0.050 to below 5.0 $\mu g$/eye, or about 0.10 to 4.5 $\mu g$/eye, or about 0.50 to 2.5 $\mu g$/eye, or about 1.0 to 2.0 $\mu g$/eye. In still another embodiment of this invention, the three isopropyl ester compounds disclosed herein before are topically applied in a dosage range of about 0.050 to 0.750 $\mu g$/eye, preferably about 0.075 to 0.250 $\mu g$/eye, more preferably about 0.100 to 0.175 $\mu g$/eye.

Another family of 15-keto prostaglandins which should be useful in the practice of the present invention are 15-oxo-17-phenyl-18,19,20-trinor $PGF_2\alpha$ N-ethylanide and 13,14-dihydro-15-oxo-17-phenyl-18,19,20-trinor $PGF_2\alpha$ N-ethylamide. The low dosage contemplated herein for these compounds is below 15 $\mu g$/eye to as low as 0.05 $\mu g$/eye. In another embodiment of this invention, these two compounds are topically applied to the eye in a dosage of about 10 $\mu g$ to 0.10 $\mu g$/eye, or about 8 $\mu g$ to 0.50 $\mu g$/eye, or about 6 $\mu g$ to 1 $\mu g$/eye. See U.S. Pat. No. 5,352,708 and U.S. Pat. No. 6,037,364 for the corresponding 15-OH compound, 17-phenyl-18,19,20 trinor $PGF_2\alpha$ N-ethylamide, which has a clinical (daily) dose (FDA approved dose) of one drop of a 0.030% solution. As of this writing the clinical dosage of this compound is not known by the applicant; however, with typical drop sizes of about 20 to 50 $\mu l$, most usually about 30 to 35 $\mu l$, the dosage is estimated at about 6 to 15 $\mu g$/eye, probably about 9 $\mu g$/eye.

Variations of the present invention will be apparent to the skilled artisan. For example, when 15-keto latanoprost or another 15-keto compound described herein is used in a low dose maintenance regimen, the initial rapid IOP reduction can be obtained with known IOP reducing agents other than latanoprost, for example, Rescula®, Timolol, Alphagan, Azopt, Cosopt, Travoprost (isopropyl ester of fluprostenol), Bimatoprost and so on can be employed. Another alternative is to initially use a higher dose of 15-keto latanoprost, or of one of the other 15-keto compounds described herein. The dosages disclosed herein are for human use.

I claim:

1. A method for reducing intraocular pressure or for treating glaucoma which comprises topically applying to a human as an ocular eye drop a compound selected from the group consisting of 15-oxo-17-phenyl-18,19,20 trinor $PGF_2\alpha$ N-ethylamide and 13,14-dihydro-15-oxo-17-phenyl-18,19,20-trinor $PGF_2\alpha$ N-ethylamide.

2. The method of claim 1 wherein the dose is about one-tenth the usual dose of the corresponding 15-OH compound.

3. The method for maintaining a reduced intraocular pressure by periodic administration to a human as a topically applied ocular eye drop, an effective amount of a compound selected from the group consisting of 15-oxo-17-phenyl-18,19,20 trinor $PGF_2\alpha$ N-ethylamide and 13,14-dihydro-15-oxo-17-phenyl-18,19,20-trinor $PGF_2\alpha$ N-ethylamide.

4. The method of claim 3, wherein the compound is applied one or two times a day.

5. The method of claim 1 wherein the dose is about 0.05 to 15 $\mu g$ per eye.

6. The method of claim 5 wherein the dose is about 0.10 to 10 $\mu g$ per eye.

7. The method of claim 6 wherein the dose is is about 0.50 to 8.0 $\mu g$ per eye.

8. The method of claim 7 wherein the dose is about 1.0 to 6.0 $\mu g$ per eye.

9. The method of claim 3 wherein the dose is about 0.05 to 15 $\mu g$ per eye.

10. The method of claim 9 wherein the dose is about 0.10 to 10 $\mu g$ per eye.

11. The method of claim 10 wherein the dose is about 0.50 to 8.0 $\mu g$ per eye.

12. The method of claim 11 wherein the dose is about 1.0 to 6.0 $\mu g$ per eye.

13. The method of claim 3 wherein the compound is applied one or two times a day.

14. The method of claim 3 wherein the intraocular pressure is initially reduced by application of a 15-OH compound.

15. A method for reducing intraocular pressure or for treating glaucoma which comprises topically applying to a human as an ocular eye drop a compound selected from the group consisting of 15-oxo-16-(3-trifluoromethylphenoxy)-17,18,19,20-tetranor $PGF_2\alpha$ isopropyl ester and 13,14-dihydro-15-oxo-16-(trifluoromethyl phenoxy)-17,18,19,20-tetranor $PGF_2\alpha$ isopropyl ester in a dose below the known dose for the corresponding 15-OH compound.

16. A method for reducing intraocular pressure or for treating glaucoma which comprises topically applying to a human as an ocular eye drop a compound selected from the group consisting of 15-oxo-16-(3-trifluoromethyl phenoxy)-

17,18,19,20-tetranor $PGF_2\alpha$ isopropyl ester and 13,14-dihydro-15-oxo-16-(trifluoromethyl phenoxy)-17,18,19,20-tetranor $PGF_2\alpha$ isopropyl ester in a dose of about 0.050 to below 5.0 μg per eye.

17. A method for maintaining a reduced intraocular pressure by periodic administration to a human as a topically applied ocular eye drop, an effective amount of a compound selected from the group consisting of 15-oxo-16-(3-trifluoromethyl phenoxy)-17,18,19,20-tetranor $PGF_2\alpha$ isopropyl ester and 13,14-dihydro-15-oxo-16-(trifluoromethyl phenoxy)-17,18,19,20-tetranor $PGF_2\alpha$ isopropyl ester.

* * * * *